US00PP27349P3

(12) United States Plant Patent
Austin

(10) Patent No.: US PP27,349 P3
(45) Date of Patent: Nov. 8, 2016

(54) ***ROSA HYBRIDA* SHRUB NAMED 'AUSWEATHER'**

(50) Latin Name: *Rosa hybrida*
Varietal Denomination: AUSweather

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 120 days.

(21) Appl. No.: 14/544,324

(22) Filed: Dec. 23, 2014

(65) Prior Publication Data
US 2016/0066485 P1 Mar. 3, 2016

(51) Int. Cl.
*A01H 5/02* (2006.01)

(52) U.S. Cl.
USPC ..... Plt./107

(58) Field of Classification Search
USPC ..... Plt./107
See application file for complete search history.

*Primary Examiner* — Anne Grunberg
(74) *Attorney, Agent, or Firm* — KPPB LLP

(57) ABSTRACT

A variety of rose plant of the shrub class, named 'AUSweather'. The 'AUSweather' is a variety of a rose suitable for cut-flower production with double, pink blooms with many petals in a quartered formation, along with a long vase life and fragrance.

1 Drawing Sheet

Classification: The present invention relates to a new *Rosa hybrida* shrub of the market class 'English Rose'.

Variety denomination: The new plant has the varietal denomination 'AUSweather'.

CROSS-REFERENCE TO RELATED APPLICATION

The present application claims priority to European CPVO 2014/2104, filed Aug. 28, 2014.

ORIGIN OF INVENTION

This invention relates to a new and distinct variety of shrub rose plant named 'AUSweather', which was originated from the cross-pollination of the two 'unnamed' and unpatented seedlings of *Rosa hybrida.*

BACKGROUND OF THE INVENTION

The primary objective of this breeding was to produce a rose variety suitable for cut-flower production with double, pink blooms with many petals arranged in a quartered formation, along with a long vase life and fragrance.

SUMMARY OF THE INVENTION

Among the features which distinguish the new variety from others presently available and commercial rose cultivars known to the inventor is the following combination of characteristics: pink roses on strong stems with many-petalled blooms that are arranged in a quartered formation.

Asexual reproduction of the new variety by budding as performed at Bowling Green Lane in Albrighton, Britain shows that the foregoing and other distinguishing characteristics come true to form and are established and transmitted through succeeding asexual propagations. 'AUSweather' may be asexually propagated by budding. The budding successfully occurred on the plant/rootstock *Rosa* 'Inermis' for the observed plants.

COMPARISON WITH PARENTS

The seed and pollen parents of 'AUSweather' are two unnamed seedlings. The new rose may be distinguished from its seed parent, by the following combination of characteristics: the seed parent has a flower which is pink in the center, but which fades almost to white at the edges, whereas 'AUSweather' blooms are more uniformly pink. In addition, the seed variety is not quartered. The new rose may be distinguished from its pollen parent, by the following combination of characteristics: the parent is red and has far fewer petals than 'AUSweather'.

COMPARISON WITH THE CLOSEST COMMERCIALLY AVAILABLE CULTIVAR

The closest commercially available cultivar to the new variety is the 'AUSimmon' (U.S. Plant Pat. No. 17,267). The new rose may be distinguished from the 'AUSimmon' variety by the following combination of characteristics: the 'AUSimmon' has a bloom size which is much larger (12 cm) than the bloom size of the 'AUSweather' (9 cm). The blooms of 'AUSimmon' also have more petals (120 per bloom) to the blooms of 'AUSweather' (92 per bloom). In addition, 'AUSimmon' has blooms that have outer petals that are tinged green whereas 'AUSweather' is uniformly pink.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSweather' specimens were made at the nursery at David Austin Roses Limited in Albrighton, Wolverhampton, United Kingdom. The following description is of 5 year-old potted rose plants of the new variety grown indoors in a greenhouse in Albrighton, Britain in the month of June. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 2.3 cm long and 2 cm in diameter when the petals start to unfurl.

*Form*.—The bud form is broad based.

*Color*.—When sepals first divide, the bud color is RHS 38A (red group). When half blown, the upper sides of the petals are RHS 73C (red-purple group), and the lower sides of the petals are RHS N74D (red-purple group).

*Calyx*.—Shape: star-shaped when the bloom is open and folding back against the stem. Length: 4 cm. Diameter: 2.2 cm.

*Sepals*.—Arrangement: Regularly arranged. Color: Upper Surface: green RHS 148C (yellow-green group). Lower Surface: green RHS 144A (yellow-green group). Length: 4 cm. Width: 1.2 cm. Shape: Lanceolate. Surface texture: Upper Surface: Downy. Lower Surface: Glandular. Number: There are 3 normally appendaged sepals, and 2 unappendaged sepals with hairy edges.

*Receptacles*.—Color: RHS 144A (yellow-green group). Shape: funnel. Size: small, about 1 cm high× 0.8 cm wide. Surface: Smooth.

*Peduncle*.—Length: medium, averaging about 8 cm. Surface: Smooth. Color: RHS 144A (yellow-green group). Strength: Strong.

Blooms:

*Size*.—Large, average open diameter is about 9 cm.

*Borne*.—Singly. (Note: the inflorescence when the shrub is growing naturally may hold between 1-4 blooms, and then has a rounded shape. When grown commercially for cut-flower production the stems are disbudded to ensure the blooms are grown singly.)

*Stems*.—Strength: Strong, average length is about 95 cm. Diameter: 6 mm.

*Form*.—When first open, bloom is cupped. Permanence of bloom: retains its form to the end.

Petalage: Number of petals under normal conditions: 92.

*Color*.—The upper sides of the petals are RHS 65B (red-purple group). The reverse sides of the petals are RHS 67C (red-purple group). The base of the outer petals has a small yellow spot RHS 2D (yellow group) on the inner side and RHS 2C (yellow group) on the outer side.

*Variegations*.—None.

*Discoloration*.—The general tonality at the end of the first day is RHS 68A (red-purple group), and at the end of the third day is RHS 68A (red-purple group).

*Fragrance*.—Moderate. Character of fragrance: rose.

Petals:

*Texture*.—Smooth.

*Size*.—Width: 4.2 cm. Length: 5.5 cm.

*Surface*.—Smooth.

*Shape*.—Obovate.

*Margin*.—Entire but wavy, with very few incisions and very little undulation or reflexing.

*Apex shape*.—Rounded.

*Base shape*.—Acute.

*Form*.—Incurved.

*Arrangement*.—Quartered.

*Petaloids*.—Number: many, around 12. Color: RHS 67A (red-purple group). Length: 2.3 cm. Width: 1 cm. Shape: Obovate (folded). Margin: Uniform.

*Persistence*.—Petals hang on and dry.

*Lastingness*.—On the plant: not tested. As a cut flower: About 6 days.

Reproductive parts:

*Stamens*.—Number: around 70. Length: 14 mm.

*Anthers*.—Length: 3.5 mm. Color: RHS 11A (yellow group). Arrangement: Mixed with petaloids.

*Filaments*.—Color: RHS 11A (yellow group). Length: 11 mm.

*Pollen*.—Color: RHS 20A (yellow-orange group).

*Pistils*.—Number: 40. Length: 18 mm.

*Styles*.—Color: RHS 58C (red-purple group) and N155C (white group). Length: 17.5 mm.

*Stigmas*.—Color: RHS 16B (yellow-orange group). Length: 0.5 mm.

*Hips*.—None Observed.

PLANT CHARACTERISTICS

Plant form: Shrub.

Plant growth: Medium.

Age to maturity: One year.

Mature plant: Height: 1 m 20 cm. Width: 90 cm.

Rootstock: *Rosa* 'Inermis' for the observed plants.

Foliage:

*Number*.—Leaflets on normal mid-stem leaves is: 3 and 5 (including terminal leaflet).

*Size*.—Large, about 12 cm long×9 cm wide.

*Quantity*.—Normal. Number of leaves per flowering stem is: 6.

*Color*.—New foliage: Upper side: RHS 146A (yellow-green group). Lower side: RHS 182A (greyed-red group) with RHS 146B (yellow-green group). Old foliage: Upper side: RHS 147A (yellow-green group). Lower side: RHS 147B (yellow-green group).

Leaflets:

*Size*.—About 5.8 cm long×4 cm wide.

*Shape*.—Ovate.

*Base shape*.—Rounded.

*Apex shape*.—Acuminate.

*Texture*.—Smooth.

*Edge*.—Serrated.

*Serrations*.—Single.

*Petiole*.—Color: RHS 146A (yellow-green group). Length: 3.4 cm. Width: 1.8 mm. Surface Texture: Glandular.

*Petiole rachis*.—Color: RHS 146A (yellow-green group). Underside: with prickles.

*Stipules*.—Length: 2 cm, glandular. Color: RHS 144A (yellow-green group).

*Auricle*.—Shape: Lanceolate. Length: 6 mm. Width: 0.8 mm. Color: RHS 144A (yellow-green group).

*Vein color*.—Same as leaf color.

*Venation pattern*.—Reticulate.

Wood:

*New wood*.—Color: RHS 184C (greyed-purple group). Bark: Smooth.

*Old wood*.—Color: RHS 146B (yellow-green group). Bark: Smooth.

Branching habit:

*Number*.—None.

Stems:

*Mature stem*.—Length: 95 cm. Diameter: 6 mm.

*Internode distance*.—6 cm. The above measurements are all variable, depending on growing conditions in a season.

*Stem pubescence present*.—No.

Prickles:

*Quantity*.—On main canes from base: Ordinary. Number per stem length: 6 per 10 cm.

*Form*.—Deep concave.

*Length*.—7 mm.

*Color when young*.—RHS 180B (greyed-red group).

*Color when mature*.—RHS 183D (greyed-purple group).

Small prickles:

*Quantity*.—Main stalk: None. Laterals: None.

Disease resistance:

*Mildew*.—Resistant.

*Blackspot*.—Not tested.

*Rust*.—Not tested.

Pest resistance: Not tested.

Winter hardiness: Not tested.

Growing conditions: Normal greenhouse conditions.

What is claimed is:

1. A new and distinct variety of rose plant of the shrub class suitable for cut flower production, substantially as herein shown and described.

* * * * *

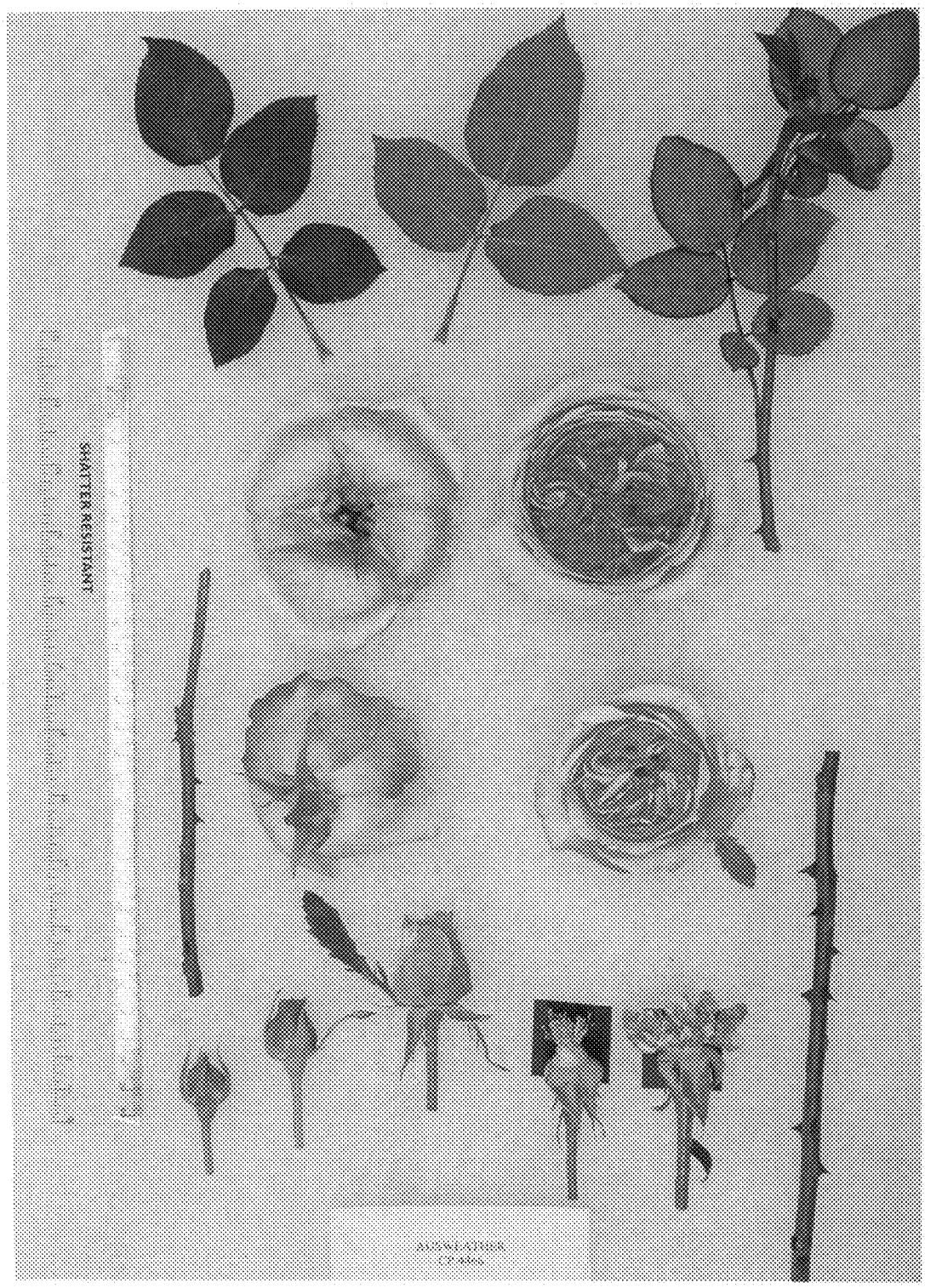
SHATTER RESISTANT